United States Patent [19]

Radkins et al.

[11] 4,347,217
[45] Aug. 31, 1982

[54] INCENSE HOLDER

[75] Inventors: Andrew P. Radkins, Bartlett; David P. Macarus, Downers Grove; James A. Radkins, Chicago; Jay S. Waxman, Skokie, all of Ill.

[73] Assignee: Genieco Inc., Chicago, Ill.

[21] Appl. No.: 151,202

[22] Filed: May 19, 1980

[51] Int. Cl.³ .............................................. A61L 9/03
[52] U.S. Cl. ........................................ 422/126; 422/4; 422/305; 422/306; 431/296
[58] Field of Search .................. 422/4, 126, 305, 306; 431/296; D23/78; 43/125, 127, 129

[56] References Cited

U.S. PATENT DOCUMENTS

| D. 234,465 | 3/1975 | Warner | D23/78 |
|---|---|---|---|
| 240,384 | 4/1881 | Carey | 422/126 |
| 775,159 | 11/1904 | Womble . | |
| 1,212,903 | 1/1917 | Cherry . | |
| 1,412,516 | 4/1922 | Ghosh | 422/126 |
| 1,530,103 | 3/1925 | Booth . | |
| 1,609,814 | 12/1926 | Gray et al. | 422/126 |
| 2,770,854 | 11/1956 | Miszeika . | |
| 4,099,916 | 7/1978 | Gardner et al. | 422/126 |
| 4,155,979 | 5/1979 | Powell | 422/126 |

Primary Examiner—Barry S. Richman
Attorney, Agent, or Firm—Dithmar, Stotland, Stratman & Levy

[57] ABSTRACT

An incense holder includes a base having a central upstanding projection with an axial bore therein for receiving the lower end of a rod adapted to be passed through the holes in a plurality of incense beads. The rod includes a mounting portion shaped to cooperate with the bore for holding the rod uptight, and a stop portion for maintaining a space between the incense beads and the base. The bore may also receive an incense stick. Several forms of base are disclosed, some adapted for supporting spiral incense carriers thereon. Two forms of rod mounting portions are disclosed.

9 Claims, 17 Drawing Figures

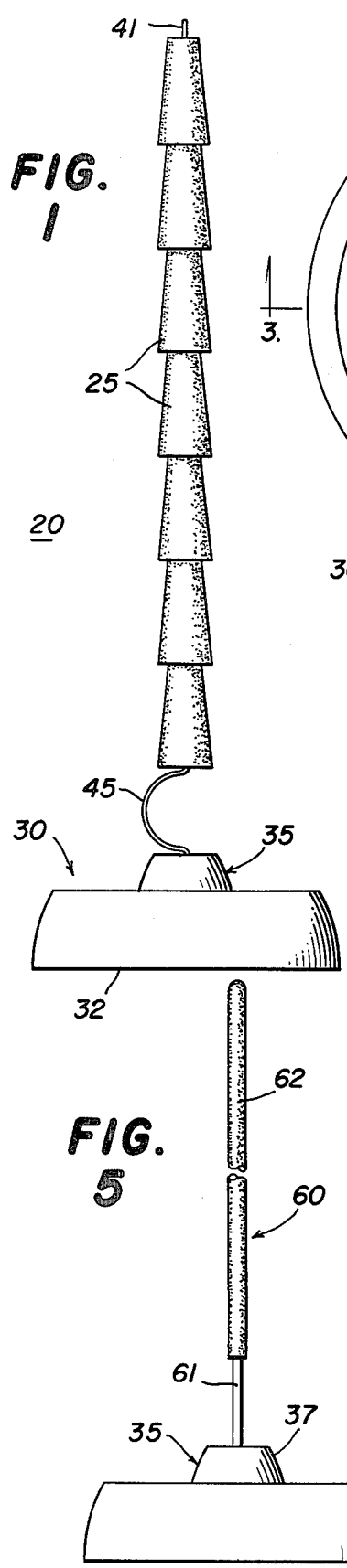
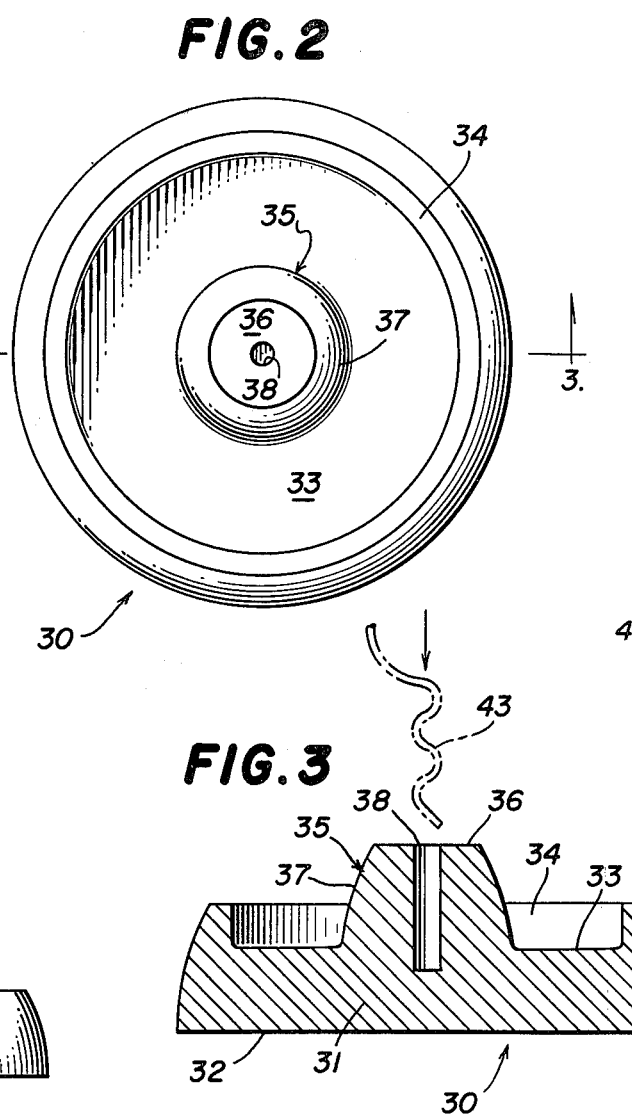
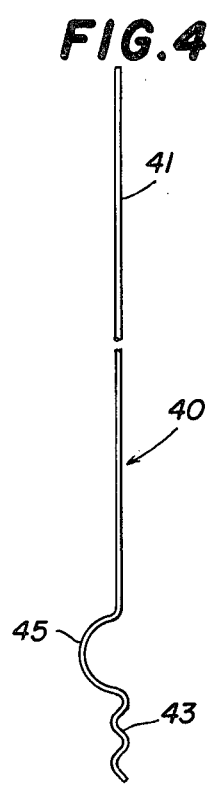
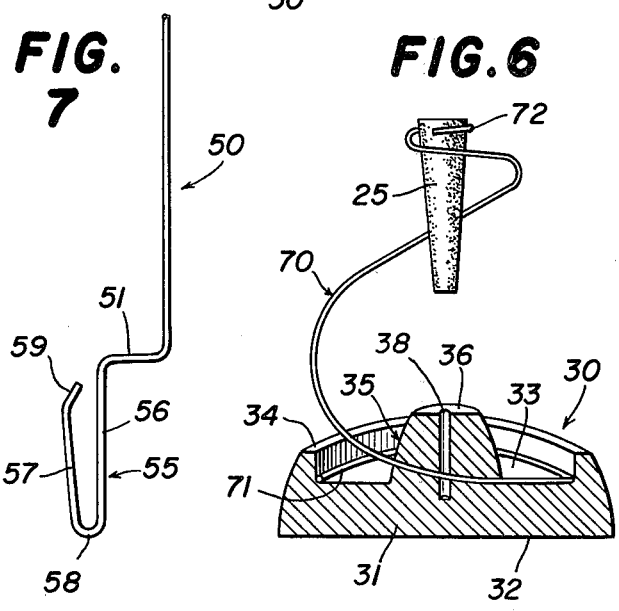

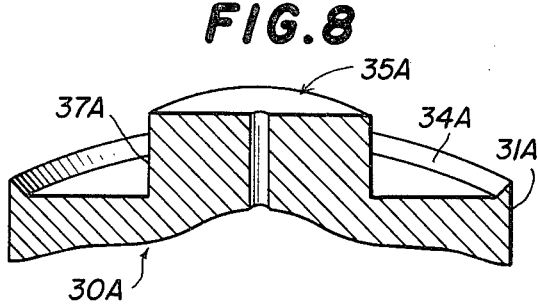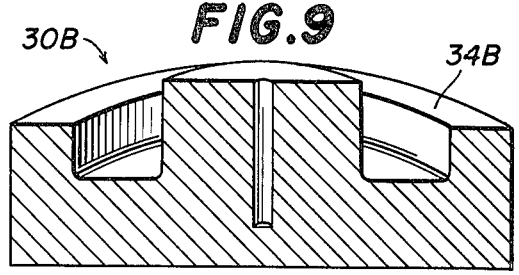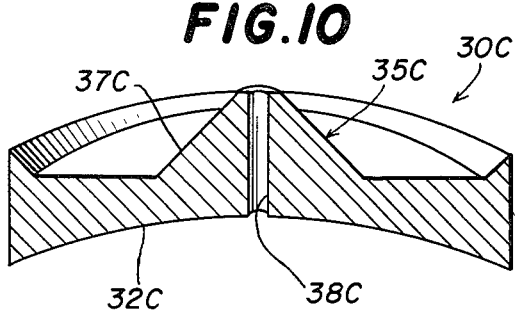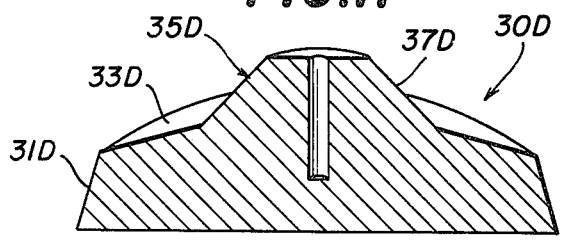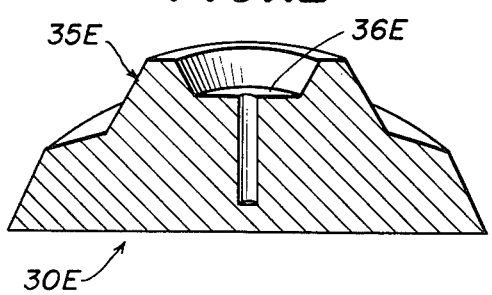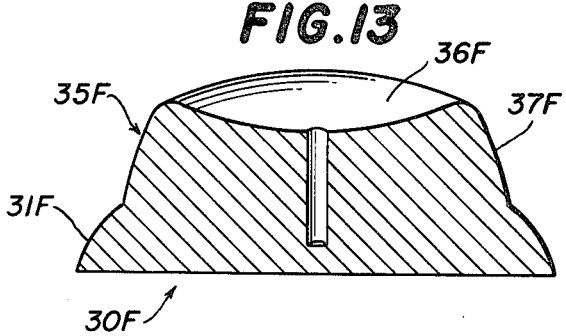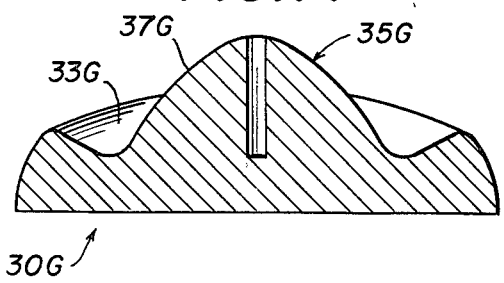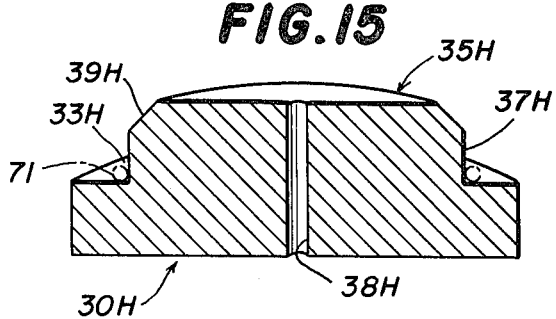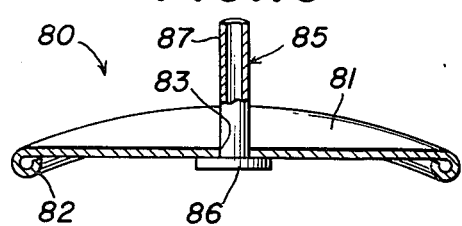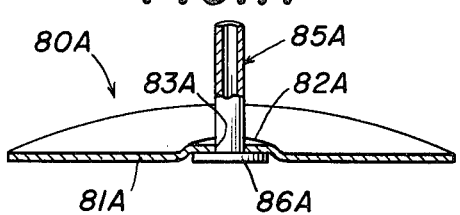

INCENSE HOLDER

BACKGROUND OF THE INVENTION

The present invention relates to holders for burning incense products, particularly beaded incense.

In U.S. Pat. No. 4,099,916, there is disclosed a beaded incense product which comprises a plurality of incense beads, each being a solid body with a hole therethrough and a rod which passes through a selected number of the beads to provide a stand therefor, the lower end of the rod being bent to form a base for the stand. While this wire rod stand effectively serves to support the incense beads for burning thereof, it does not serve to protect the underlying support surface on which the stand is mounted. Thus, if the stand is mounted on a table, for example, ashes and the like are free to fall on the table surface, and as the bottommost incense bead is burned, the heat thereof may tend to scorch, discolor or otherwise damage the support surface.

Furthermore, the wire rod stand is relatively unstable and, because of its light weight, may easily be tipped over.

Finally, the wire rod stand of the '916 patent is adaptable only for use with beaded incense and does not serve to support other types of incense products.

SUMMARY OF THE INVENTION

It is therefore an important object of the present invention to provide an incense holder which will support a plurality of incense beads in a stable upright position.

It is another object of this invention to provide an incense holder which will provide a tray-like base to catch particulate debris from the burning of the incense and to insulate the burning incense from the underlying support surface.

Another object of this invention is to provide an incense holder which is suitable for supporting thereon several different types of incense product in several forms of incense carriers.

These and other objects of the invention are attained by providing an incense holder comprising a body having a bottom wall with at least a portion thereof being adapted to rest upon an associated underlying support surface, an upstanding projection extending upwardly from the bottom wall centrally thereof, and an elongated bore extending downwardly through the projection centrally thereof and adapted to receive therein the lower end of an associated elongated incense-carrying member.

Further features of the invention pertain to the particular arrangement of the parts of the incense holder whereby the above-outlined and additional operating features thereof are attained.

The invention, both as to its organization and method of operation, together with further objects and advantages thereof, will best be understood by reference to the following specification taken in connection with the accompanying drawings.

BRIEF DESCRIPTION OF THE DRAWINGS

FIG. 1 is a side elevational view of an incense holder constructed in accordance with and embodying the features of a first embodiment of the present invention;

FIG. 2 is an enlarged top plan view of the base of the incense holder of FIG. 1;

FIG. 3 is a view in vertical section taken along the line 3—3 in FIG. 2;

FIG. 4 is a side elevational view of the incense carrier rod of the incense holder of FIG. 1;

FIG. 5 is a view, similar to FIG. 1, illustrating the base of the incense holder used for supporting stick incense;

FIG. 6 is a perspective view in vertical section of the base of the incense holder of FIG. 1, illustrating the use thereof for supporting a spiral wire incense carrier;

FIG. 7 is a fragmentary side elevational view of the lower end of a second embodiment of the beaded incense carrier rod according to the present invention.

FIGS. 8 through 15 are enlarged views, similar to FIG. 6, illustrating several different embodiments of base for the incense holder of FIG. 1;

FIG. 16 is a side elevational view in partial vertical section of still another embodiment of base for the incense holder of the present invention; and FIG. 17 is a view similar to FIG. 16 illustrating a modified form of the base of FIG. 16.

DESCRIPTION OF THE PREFERRED EMBODIMENTS

Referring to FIGS. 1 through 4 of the drawings, there is illustrated an incense holder, generally designated by the numeral 20, particularly adapted for supporting a plurality of incense beads 25. Each of the incense beads 25 is generally frustoconical in shape, with an axial hole extending therethrough, but it will be appreciated that incense beads may be provided in any of a number of different shapes, as is explained in detail in the aforementioned U.S. Pat. No. 4,099,916.

The incense holder 20 includes a base, generally designated by the numeral 30, and an incense bead carrier rod, generally designated by the numeral 40. The base 30 is generally circular in shape and includes a circular bottom wall 31 having a flat circular bottom surface 32 and an annular top surface 33 substantially parallel to the bottom surface 32. Integral with the bottom wall 31 and extending upwardly therefrom around the entire perimeter of the top surface 33 is an upstanding annular rim 34. Integral with the bottom wall 31 and projecting upwardly therefrom centrally thereof and extending a predetermined distance above the top of the rim 34 is a projection 35 having a flat circular top surface 36. The projection 35 is generally in the shape of a truncated dome and has a convex outer surface 37 and is provided with an axial mounting bore 38 extending centrally therethrough from the top surface 36 thereof downwardly into the bottom wall 31. It will be appreciated that the annular top surface 33 of the base 30 cooperates with the rim 34 and the projection 35 to form a shallow annular tray-like recess.

The base 30 is preferably formed of a nonflammable heat-resistant material such as plaster, clay, porcelain or the like, but it will be appreciated that it could be formed of any desired material, such as metal, wood or plastic.

The carrier rod 40 is preferably formed of a metal wire having a diameter substantially less than the diameter of the mounting bore 38 in the base 30. The rod 40 has a straight, elongated carrying portion 41, and is provided at one end thereof with a serpentine mounting portion 43 which comprises a plurality of generally sinusoidal convolutions having a peak-to-peak amplitude very slightly greater than the diameter of the mounting bore 38 in the base 30. Separating the carrying portion 41 from the serpentine mounting portion 43 is a generally semicircular, laterally offset stop portion 45. The rod 40 is preferably formed of a noncorroding and oxidation-resistant metal such as stainless steel.

In use, the mounting portion 43 of the rod 40 is inserted into the mounting bore 38 of the base 30, the convolutions of the mounting portion 43 being dimensioned so as to snugly frictionally fit in the bore 38, thereby to prevent wobbling of the rod 40 therein and support the rod 40 in a substantially stable upright position. In this regard, it will be noted that the added height afforded by the projection 35 permits the mounting bore 38 to be of sufficient length to insure a stable mounting of the rod 40 therein. One or more incense beads 25 are then threaded onto the carrying portion 41 of the rod 40, the stop portion 45 serving to limit the downward movement of the incense beads 25 along the rod 40 and effectively spacing the beads 25 a predetermined distance from the base 30. The incense beads may then be ignited and burned in the usual manner, as is more fully explained in the aforementioned U.S. Pat. No. 4,099,916.

It will be noted that the annular tray-like recess formed by the top surface 33 of the base 30 serves to catch any debris which may fall from the burning incense, and thereby protect the underlying support surface. While the base 30 is preferably formed of a heat-resistant material, such materials may, nevertheless, be subject to discoloration if they come too close to the burning incense bead. Such discoloration could result solely from the heat of the burning incense or from the condensation of perfume oils from the burning incense, or from a combination of these factors resulting in charring of the oil condensate. It will be appreciated that the stop portion 45 serves to space the incense beads 25 a sufficient distance from the base 30 to prevent such discoloration or other damage to the base 30. By reason of this spacing, the base 30 could even be formed of non-heat-resistant materials, as explained above.

Referring to FIG. 7 of the drawings, there is illustrated an alternative form of carrier rod, generally designated by the numeral 50, which is provided adjacent to one end thereof with a laterally extending stop portion 51, integral at the outer end thereof with a downwardly extending generally U-shaped mounting portion 55. More specifically, the mounting portion 55 comprises a pair of spaced-apart legs 56 and 57 interconnected at the lower ends thereof by a bight portion 58, the leg 57 being provided at its distal end with an inturned tip 59. Preferably, the lower end of the mounting portion 55 has a width slightly less than the diameter of the mounting bore 38 in the base 30, while the upper end of the mounting portion 55 has a maximum width slightly greater than the diameter of the mounting bore 38.

In use, the U-shaped mounting portion 55 is inserted into the mounting bore 38, providing a resilient frictional fit therein securely to hold the rod 50 in a stable, upright position. The inturned tip 59 of the mounting portion 55 serves to facilitate removal of the rod 50 from the bore 38 without snagging therein.

It is a significant feature of the present invention that the base 30 is adapted for supporting other types of incense products. Thus, referring to FIG. 5 of the drawings, it will be seen that the base 30 could be used for supporting stick incense, generally designated by the numeral 60. Such incense includes an elongated stick 61, the upper portion of which is coated with a layer of incense 62. In use, the uncoated lower end of the stick 61 is inserted into the mounting bore 38 for supporting the sticks incense 60 in an upright position.

Referring to FIG. 6, it can be seen that the base 30 could also be used for supporting a spiral-type wire incense carrier, generally designated by the numeral 70. Such spiral carriers are known in the art, and, in use, the wide base coil 71 of the spiral is fitted into the tray-like recess, in surrounding relationship with the projection 35 and resiliently urged outwardly against the inner surface of the annular rim 34. The carrier 70 may then be used to support a cone-shaped incense bead 25 or other type of incense block above the base 30. If desired, the base coil 71 may be adhesively secured to the base 30. Preferably, the thus preassembled incense burner has a total height greater than that of the carton in which it is packaged, so as resiliently to hold the base in place in the carton.

While the rod 40 is preferably formed of metal, it will be appreciated that it could also be formed of bamboo or other type of consumable material. In this regard, another feature of the present invention is that, instead of the rod 40, any suitable type of bead holder, such as a toothpick, an hors d'oeuvre stick, a paper clip or the like could be used for supporting incense beads on the base 30. Additionally, individual beads 25 of incense could be placed on the top surface 33 of the base 30 and burned in the tray-like recess formed thereby, if desired.

Referring now to FIGS. 8 through 15 of the drawings, there is illustrated a plurality of alternative forms of the base 30, each of these forms being of integral one-piece construction and having a central projection extending upwardly therefrom with an axial bore therethrough. In FIG. 8 there is illustrated as base 30A which is generally similar in shape to the base 30, except that the outer circumferential surface 31A of the bottom wall is a right circular cylinder. Projecting above the top surface of the base around the entire perimeter thereof is a short rim 34A which is beveled upwardly and outwardly. The central projection 35A has a right circular cylindrical outer surface 37A.

In FIG. 9 there is illustrated a base 30B which is similar in construction to the base 30A, except that it is provided with a thick flat-topped annular rim 34B around the perimeter of the top surface of the base.

The base 30C illustrated in FIG. 10 is similar to the base 30A, with the exception that the bottom wall is provided with a concave bottom surface 32C, and the upstanding projection 35C has a frustoconical outer surface 37C. The central bore 38C through the projection 35C extends all the way from the top thereof to the bottom surface 32C. The space beneath the base 30C formed by the concave bottom surface 32C serves as an additional thermal insulation to prevent scorching or other damage to the underlying support surface, the length of the bore 38C being such that when the rod 40 is mounted therein the lower end thereof is spaced above the underlying support surface.

In FIG. 11 there is illustrated a base 30D, the bottom wall of which has a generally frustoconical outer peripheral surface 31D. The base 30D has a gently upwardly and inwardly sloping frustoconical top surface 33D which joins a projection 35D having a frustoconical outer surface 37D which has a more gentle slope than that of the projection 35C.

FIG. 12 illustrates a base 30E which is generally similar to the base 30D, except that the upstanding projection 35E is somewhat wider than the projection 35D, and is provided with a circular recessed portion 35E in the top thereof.

The base 30F, illustrated in FIG. 13, has a bottom wall with a rounded, convex outer surface 31F, the upper edge of which joins the lower end of the central projection 35F, which also has a rounded convex outer surface 37F. Formed in the top of the projection 35F is a shallow recess defining a concave top surface 36F.

In FIG. 14 there is illustrated a base 30G, the bottom wall of which has an annular, generally concave top surface 33G, the inner margin of which is continuous with the convex rounded outer surface 37G of a generally dome-shaped central projection 35G.

In FIG. 15 there is illustrated a base 30H, which is generally similar to the base 30A, except that there is no peripheral rim at the outer edge of the top surface 33H, and the central projection 35H is of enlarged diameter, having a right circular cylindrical outer surface 37H, provided with a chamfered portion 39H at the upper end thereof. The mounting bore 38H extends entirely through the base 30H.

As explained above in connection with FIG. 6, a spiral wire incense carrier can be supported by the base 30 by slightly compressing the base coil 71 and having it resiliently urged into frictional engagement with the inner surface of the rim 34. It will be appreciated that such a spiral carrier could also be supported on a rimless base such as that illustrated in FIG. 15 where the diameter of the base coil 71 is slightly less than the diameter of the upstanding projection 35H. Thus, a slight expansion of the base coil 71 of the spiral carrier will permit it to be fitted over the projection 35H and resiliently snugly held in engagement with the outer surface 37H thereof, as illustrated in FIG. 15.

Referring to FIG. 16 of the drawings, there is illustrated another embodiment of base for the present invention, generally designated by the numeral 80, which is preferably formed of light-gauge metal. The base 80 includes a generally circular flat base plate 81, the peripheral edge of which is rolled under to form a depending rolled rim 82. Formed centrally of the base plate 81 is a small circular aperture 83 for accommodating a projection, generally designated by the numeral 85. More specifically, the projection 85 includes a small circular foot 86 disposed in use beneath the base plate 81 and fixedly secured to an upstanding tube 87 which extends upwardly through the aperture 83 and projects a predetermined distance above the base plate 81. The projection 85 is fixedly secured to the base plate 81, as by welding or the like.

In use, the carrier rod 40 or 50 is inserted into the tube 87 for holding one or more incense beads 25 thereon, in the same manner as was described above with respect to FIGS. 1 through 4 and 7. The base 80 could, also, be used for supporting stick incense in the manner illustrated above with respect to FIG. 5. Preferably, the thickness of the rolled rim 82 is greater than that of the projection foot 86 so that the foot 86 remains out of contact with the underlying support surface and will not scratch or mar it in any way.

Referring to FIG. 17, there is a modified form of the base 80, generally designated by the numeral 80A. The base 80A is also provided with a circular base plate 81A, but instead of having a rolled peripheral rim, the base plate 81A is provided with a raised circular boss 82A centrally thereof, in which is formed a central aperture 83A. The boss 82A is shaped and dimensioned to receive therein the foot 86A of the projection 85A so that the bottom surface of the foot 85A is substantially flush with the bottom surface of the base plate 81A. The tube of the projection 85A extends upwardly through the aperture 83A, and the projection 85A is secured to the base plate 81A in the same manner as was described above with respect to FIG. 16.

Preferably, the bases 80 and 80A are formed of aluminum. The base plate 81A of the base 80A could also be formed of an embossed paperboard, which could easily be die-cut and could, if desired, be coated with metal foil, or printed with any desired decorative designs or the like.

While the bases of the incense holder 20 of the present invention have all been illustrated as being circular in shape, it will be understood that any other desired shape could be used. Similarly, the mounting bore therein could have a transverse cross-section other than circular. The stop portion 45 of the carrier rod 40 could be any desired shape or configuration as long as it is laterally offset so as to perform the intended stop function. Also, while the carrying portion 41 of the carrier rod 40 is illustrated as being straight, it will be appreciated that it could be bent into other configurations, as illustrated in the aforementioned U.S. Pat. No. 4,099,916. Furthermore, the wire of the carrier rods 40 and 50 preferably has a diameter of approximately 0.035 inches. If the wire is significantly thinner than this, it does not have sufficient strength to support a plurality of incense beads in an upright position. If the wire is significantly thicker, it acts as a heat sink and causes a significant loss of heat from the burning incense, which makes it difficult to keep the incense burning. Furthermore, if the wire is too thick, the incense beads 25 will not slide freely therealong. Preferably, the lengths of the mounting portions 43 and 55 of the carrier rods 40 and 50 are such that, when used with bases of the type illustrated in FIGS. 10 and 15, they will not contact the underlying table or other support surface.

From the foregoing, it can be seen that there has been provided an improved incense holder which permits the supporting of a plurality of incense beads in a stable, upright fashion, while serving to protect the underlying support surface from debris from the burning incense, scorching, discoloration or other damage. There has also been provided an improved incense holder of the type set forth, which permits the supporting thereon of several different types of incense products and carriers therefor.

While there have been described what are at present considered to be the preferred embodiments of the invention, it will be understood that various modifications may be made therein, and it is intended to cover in the appended claims all such modifications as fall within the true spirit and scope of the invention.

What is claimed is:

1. A carrier for incense beads having holes therethrough, said carrier comprising a rod adapted to extend through the holes of one or more associated incense beads, an axially elongated mounting portion at one end of said rod having a lateral extent greater than the thickness of said rod, and a laterally-offset stop portion adjacent to said mounting portion shaped and dimensioned to prevent the passage of associated incense beads therealong thereby to maintain a predetermined space between the associated incense beads and said mounting portion.

2. The carrier of claim 1, wherein said mounting portion is serpentine in shape comprising a plurality of convolutions.

3. The carrier of claim 1, wherein said stop portion is generally semicircular in shape.

4. The carrier of claim 1, wherein said rod is formed of stainless steel.

5. An incense holder for incense beads having holes therethrough, said holder comprising a body having a bottom wall adapted to rest upon an associated underlying support surface, an upstanding projection extending upwardly from said bottom wall centrally thereof and projecting well above the remainder of said body, and an elongated mounting bore extending downwardly through said projection centrally thereof, an elongated rod having a diameter substantially less than the diameter of said mounting bore and adapted to extend through the holes of one or more associated incense beads, an axially elongated mounting portion at one end of said rod having a lateral extent greater than the thickness of said rod and shaped and dimensioned to be received in a substantially stable upright orientation in said mounting bore, and a laterally-offset stop portion adjacent to said mounting portion shaped and dimensioned to prevent the passage of incense beads therealong and to limit the depth of insertion of said mounting portion in said mounting bore thereby to maintain a predetermined space between the incense beads and said body.

6. The incense holder of claim 1, wherein said projection is substantially cylindrical in shape.

7. The incense holder of claim 5, wherein said bottom wall has an annular top surface disposed in surrounding relationship with said projection, and further including an outer rim extending upwardly from said top surface around the entire perimeter thereof.

8. The incense holder of claim 5, wherein said body has a concave bottom surface.

9. The incense holder of claim 5, wherein said mounting portion is adapted to be resiliently frictionally held in said mounting bore.

* * * * *